US010215830B2

(12) United States Patent
Kwak et al.

(10) Patent No.: US 10,215,830 B2
(45) Date of Patent: Feb. 26, 2019

(54) AUTOMATED CANCER DETECTION USING MRI

(71) Applicant: The United States of America, as represented by the Secretary, Department of Health and Human Services, Washington, DC (US)

(72) Inventors: Jin Tae Kwak, Rockville, MD (US); Bradford J. Wood, Potomac, MD (US); Sheng Xu, Rockville, MD (US); Baris Turkbey, Rockville, MD (US); Peter L. Choyke, Rockville, MD (US); Peter A. Pinto, Bethesda, MD (US); Ronald M. Summers, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 383 days.

(21) Appl. No.: 14/971,296

(22) Filed: Dec. 16, 2015

(65) Prior Publication Data

US 2017/0176565 A1    Jun. 22, 2017

(51) Int. Cl.
*G01R 33/00* (2006.01)
*G01R 33/563* (2006.01)
(Continued)

(52) U.S. Cl.
CPC ........ *G01R 33/56341* (2013.01); *A61B 5/055* (2013.01); *A61B 5/4381* (2013.01); *G01R 33/465* (2013.01); *G01R 33/5602* (2013.01); *G06T 7/0012* (2013.01); *G06T 7/41* (2017.01); *G06T 2207/10088* (2013.01);
(Continued)

(58) Field of Classification Search
CPC .......... G01R 33/56341; G01R 33/5602; G01R 33/465; A61B 5/055; A61B 5/4381
See application file for complete search history.

(56) References Cited

U.S. PATENT DOCUMENTS

2010/0329529 A1* 12/2010 Feldman ............. G06K 9/6252
                                                           382/131
2013/0144916 A1*  6/2013 Lum ....................... G06F 19/24
                                                           707/790

FOREIGN PATENT DOCUMENTS

WO    WO 2014/080305    5/2014

OTHER PUBLICATIONS

Yang et al. ("Evaluation of tumor-derived MRI-texture features for discrimination of molecular subtypes and prediction of 12-mont survival status in glioblastoma", Medical Physics, vol. 42, Issue 11, p. 6725-6735, Oct. 29, 2015.*

(Continued)

*Primary Examiner* — Joseph M Santos Rodriguez
(74) *Attorney, Agent, or Firm* — Klarquist Sparkman, LLP

(57) ABSTRACT

Methods and systems for diagnosing cancer in the prostate and other organs are disclosed. Exemplary methods comprises extracting texture information from MRI imaging data for a target organ, sometimes using two or more different imaging modalities. Texture features are determined that are indicative of cancer by identifying frequent texture patterns. A classification model is generated based on the determined texture features that are indicative of cancer, and diagnostic cancer prediction information for the target organ is then generated to help diagnose cancer in the organ.

19 Claims, 10 Drawing Sheets

(51) Int. Cl.
   A61B 5/055    (2006.01)
   A61B 5/00     (2006.01)
   G01R 33/56    (2006.01)
   G01R 33/465   (2006.01)
   G06T 7/00     (2017.01)
   G06T 7/41     (2017.01)
(52) U.S. Cl.
   CPC ........... G06T 2207/10092 (2013.01); G06T 2207/20081 (2013.01); G06T 2207/30081 (2013.01)

(56) References Cited

OTHER PUBLICATIONS

Peng et al. ("Feature selection based on Mutual information: criteria of Max-dependency, Max-relevance and Min-Redundancy", IEEE Transactions on pattern analysis and machine intelligence. vol. 26, No. 8, p. 1226-1238, Aug. 2005).*
Guo et al. ("Local directional derivative pattern for rotation invariant texture classification", Neural Comput & Applic. DOI 10.1007/s00521-011-0586-6). 2011.*
Ojala et al. ("Multiresolution Gray-scale and rotation invariant texture classification with local binary patterns"; IEEE transactions on pattern analysis and Machine intelligence, vol. 24, No. 7, Jul. 2002.*
Kim et al. "High-b-Value Diffusion-Weighted Imaging at 3 T to detect prostate cancer:Comparisons Between b Values of 1,000 and 2,000 s/mm2" AJR 2010, 194, Jan. 2010.*
International Search Report and Written Opinion for related International Application No. PCT/US2016/066556, 10 pages, dated Mar. 21, 2017.
Giannini et al., "A fully automatic computer aided diagnosis system for peripheral zone prostate cancer detection using multi-parametric magnetic resonance imaging," *Computerized Medical Imaging and Graphics*, www.elsevier.com/locate/compmedimag, 8 pages (Sep. 2, 2015).
Grant, et al., "Comparison of calculated and acquired high b value diffusion-weighted imaging in prostate cancer," *Abdominal Imaging*, 40:578-586 (Sep. 16, 2014).
Ichikawa et al., "High-b Value Diffusion-Weighted MRI for Detecting Pancreatic Adenocarcinoma: Preliminary Results," *Abdominal Imaging*, AJR:188:409-414 (Feb. 2007).
Katahira et al., "Ultra-high-b-value diffusion-weighted MR imaging for the detection of prostate cancer: evaluation in 201 cases with histopathological correlation," *Eur Radiol*, 21:188-196 (2011).
Kitajima et al., "Clinical Utility of Apparent Diffusion Coefficient Values Obtained Using High b-Value When Diagnosing Prostate Cancer Using 3 Tesla MRI: Comparison Between Ultra-High b-Value (2000 S/Mm$^2$) and Standard High b-Value (1000 S/Mm$^2$)," *Journal of Magnetic Resonance Imaging*, 36:198-205 (Jan. 23, 2012).
Kwak et al., "Automated prostate cancer detection using T2-weighted and high-b-value diffusion-weighted magnetic resonance imaging," *The International Journal of Medical Physics Research and Practice*, 42(5):2368-2378 (May 2015).
Kwak et al., "Efficient data mining for local binary pattern in texture image analysis," *Expert Systems with Applications*, 42:4529-4539 (Feb. 2, 2015).
Litjens et al., "Computer-Aided Detection of Prostate Cancer in MRI," *IEEE Transactions on Medical Imaging*, 33(5):1083-1092 (May 2014).
Liu et al., "A prostate cancer computer-aided diagnosis system using multimodal magnetic resonance imaging and targeted biopsy labels," *Proc. of SPIE*, 8670:86701G-86701G6 (2013).
Metens et al., "What is the optimal b value in diffusion-weighted MR imaging to depict prostate cancer at 3T?" *Eur Radiol*, 22:703-709 (2012).
Muhi et al., "High-b-Value Diffusion-Weighted MR Imaging of Hepatocellular Lesions: Estimation of Grade of Malignancy of Hepatocellular Carcinoma," *Journal of Magnetic Resonance Imaging*, 30:1005-1011 (Aug. 7, 2009).
Niaf et al., "Computer-aided diagnosis of prostate cancer in the peripheral zone using multiparametric MRI," *Physics in Medicine and Biology*, 57:3833-3851 (2012).
Niaf et al., "Kernel-Based Learning from Both Qualitative and Quantitative Labels: Application to Prostate Cancer Diagnosis Based on Multiparametric MR Imaging," *IEEE Transactions on Image Processing*, 23(3):979-991 (Mar. 2014).
Ogawa et al., "High b-value diffusion-weighted magnetic resonance imaging for gallbladder lesions: differentiation between benignity and malignancy," *J. Gastroenterol*, 47:1352-1360 (Apr. 11, 2012).
Sennewald, "Innovative Technik für die Diagnose von Prostatakrebs," *Watson Elementary®*, 5 pages (date unknown).
Tamura et al., "Investigation of the optimal b-value to detect breast tumors with diffusion weighted imaging by 1.5-T MRI," *Cancer Imaging* 14:11, 9 pages (2014).
Tiwari et al., "Multi-kernel graph embedding for detection, Gleason grading of prostate cancer via MRI/MRS," *Med Image Anal.*, 17(2):219-235 (Feb. 2013).
Turkbey et al., "Is Apparent Diffusion Coefficient Associated with Clinical Risk Scores for Prostate Cancers that Are Visible on 3-T MR Images?" *Radiology*, 258(2):488-495 (Feb. 2011).
Ueno et al., "Ultra-High b-Value Diffusion-Weighted MRI for the Detection of Prostate Cancer With 3-T MRI," *Journal of Magnetic Resonance Imaging*, 38:154-160 (2013).
Vos et al., "Automatic computer-aided detection of prostate cancer based on multiparametric magnetic resonance image analysis," *Physics in Medicine and Biology*, 57:1527-1542 (Mar. 6, 2012).
Vos et al., "Computer-assisted analysis of peripheral zone prostate lesions using T2-weighted and dynamic contrast enhanced T1-weighted MRI," *Physics in Medicine and Biology*, 55:1719-1734 (Mar. 2, 2010).
Wang et al., "Computer Aided-Diagnosis of Prostate Cancer on Multiparametric MRI: A Technical Review of Current Research," Hindawi Publishing Corporation, *BioMed Research International*, vol. 2014, Article ID 789561, 11 pages (2014).

* cited by examiner

| | All datasets | Calibration | Validation |
|---|---|---|---|
| Patients | 244 | 108 | 136 |
| Age, mean (SD[a]) | 63.32 (7.63) | 63.11 (7.78) | 63.49 (7.53) |
| PSA, mean (SD) | 9.71 (10.23) | 9.40 (9.45) | 9.95 (10.84) |
| MR-identified lesions | 362 | 183 | 179 |
| Peripheral zone, n[b] (%) | 243 (67.13) | 131 (71.58) | 112 (62.57) |
| Central gland, n (%) | 119 (32.87) | 52 (28.42) | 67 (37.43) |
| Location | | | |
| Right, n (%) | 151 (41.71) | 69 (37.70) | 82 (45.81) |
| Midline, n (%) | 29 (8.01) | 16 (8.74) | 13 (7.26) |
| Left, n (%) | 182 (50.28) | 98 (53.55) | 84 (46.93) |
| Apex, n (%) | 190 (34.85) | 102 (55.74) | 88 (49.16) |
| Mid, n (%) | 142 (25.45) | 65 (35.52) | 77 (43.02) |
| Base, n (%) | 30 (7.88) | 16 (8.74) | 14 (7.82) |
| Suspicion level | | | |
| High, n (%) | 62 (17.13) | 38 (20.77) | 24 (13.41) |
| Moderate, n (%) | 274 (75.69) | 132 (72.13) | 142 (79.33) |
| Low, n (%) | 26 (7.18) | 13 (7.10) | 13 (7.26) |
| Gleason score[c] | | | |
| 7, n (%) | 73 (50.00) | 38 (48.72) | 35 (51.47) |
| 8, n (%) | 49 (33.56) | 29 (37.18) | 20 (29.41) |
| 9, n (%) | 20 (13.70) | 8 (10.26) | 12 (17.65) |
| 10, n (%) | 4 (2.74) | 3 (3.85) | 1 (1.47) |

[a] Standard deviation.
[b] Number of cases.
[c] From the biopsy samples obtained in axial plane.

FIG. 2

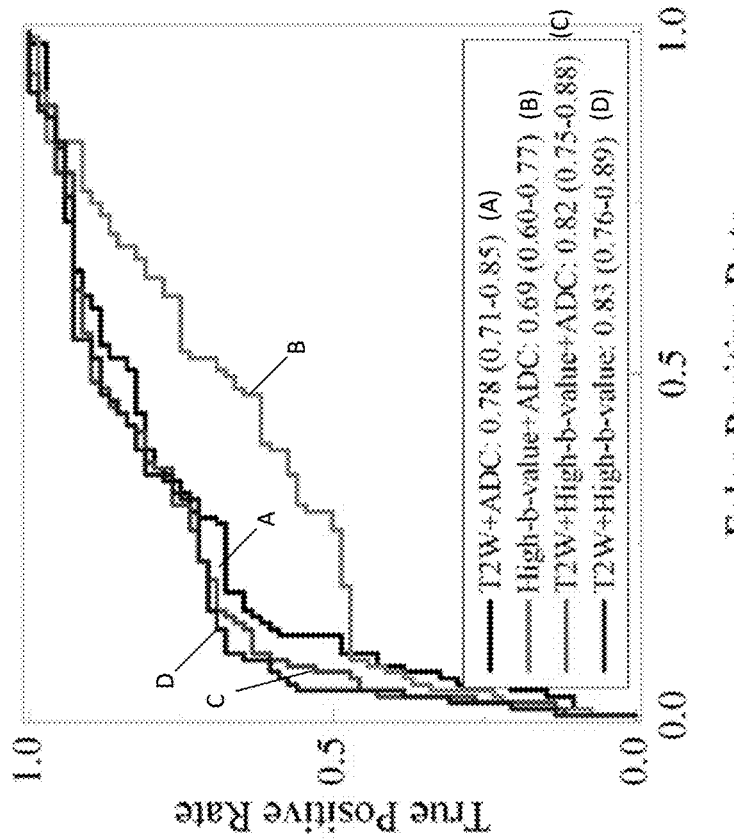
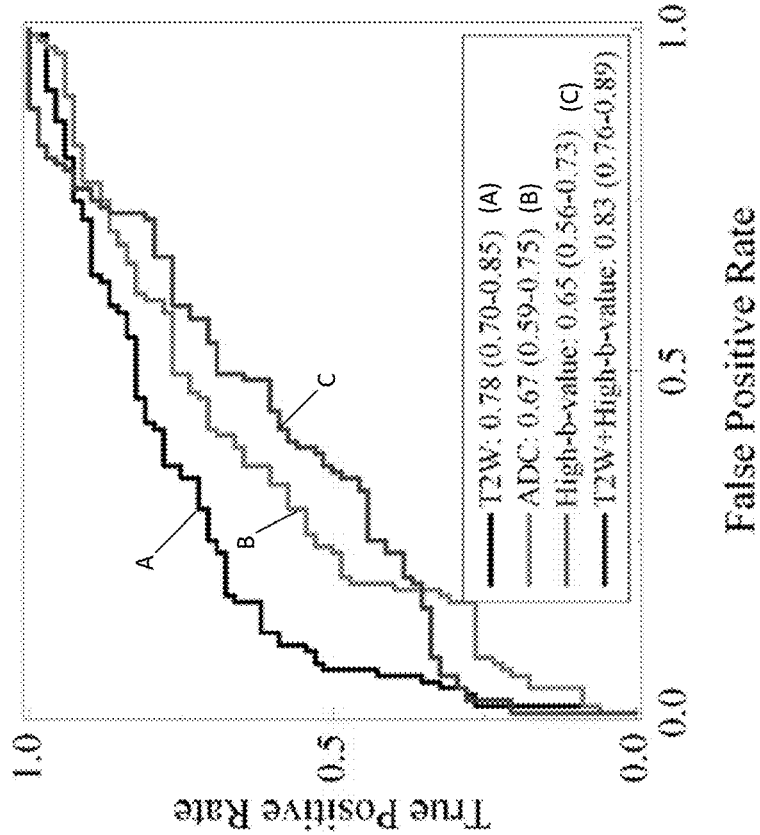
FIG. 3B
FIG. 3A

AUTOMATED CANCER DETECTION USING MRI

FIELD

This application is related to methods and systems for detecting cancer using imaging data.

BACKGROUND

Prostate cancer is the second leading cause of death from cancer in men and nearly 30,000 deaths are expected in the United States in 2014. Earlier and more accurate detection and localization of prostate cancer is critical to provide appropriate treatment. Conventional diagnosis of prostate cancer requires a biopsy. The current standard of care is to obtain 10-14 cores randomly from the prostate using ultrasound (US) imaging to guide the needle into standard anatomic locations. As a result, random biopsies lead to an overdiagnosis of incidental, nonlethal microscopic tumors and an underdiagnosis of clinically significant lesions located outside the typical biopsy template. Similar diagnosis shortcomings are also true for other forms of cancer, such as cancers of the brain, breast, colon, gallbladder, liver, and pancreas.

SUMMARY

Magnetic resonance imaging (MRI) can visualize the more aggressive lesions in the prostate, or other organs, and significantly improve the detection rate of clinically significant cancers, especially when a multiparametric MRI approach is employed. Described technologies can incorporate plural MRI sequences, such as T2-weighted (T2W) MRI, diffusion-weighted (DW) MRI, dynamic contrast enhanced (DCE) MRI, and MR spectroscopy. Described technologies can also incorporate other imaging data, such as from computed tomography, in addition to or instead of MRI data.

Identified lesions can be fused and/or superimposed on realtime US imaging to enable targeted biopsy via software-based registration or visual registration. For prostate cancer, MRI-US guided fusion biopsy can double the significant cancer detection rate compared to a standard 12-core transrectal US (TRUS) biopsy on a per-core basis and specifically lowers the detection of inconsequential, low-grade tumors. However, examining multiparametric imaging is a complex and time consuming process, requiring specific training and expertise. For example, readers are required to rapidly integrate a large amount of visual information, and mentally register and resolve sometimes contradictory findings. This process can be especially challenging to less experienced readers. Computer-aided diagnosis (CAD) systems can assist in processing multiparametric MRI by extracting and drawing attention to meaningful information contained within the images, thus, potentially facilitating or improving the decision-making.

Various different CAD systems adopting a multiparametric approach can be utilized. For example, T2W MRI can be combined with DCE MRI, diffusion-weighted imaging (DWI), and/or MR spectroscopy. Some CAD systems can incorporate T2W MRI, DCE MRI, and DWI together. Intensity and/or texture features can be used to characterize suspicious lesions. Texture features can include first-order statistics, co-occurrence matrix, gradient operators, local binary pattern, local phase quantization, and/or wavelet transform. In addition, graph embedding, random walk, locally linear embedding, and/or principal component analysis can be used to reduce data dimension and/or to improve data representation. In addition to T2W MRI and DCE MRI, and a map of apparent diffusion coefficient (ADC) from DWI can be utilized in multiparametric MRI CAD systems. In addition to these, high-b-value DWI can be utilized in multiparametric MRI CAD systems. High-b-value DWI has the capability for tissue and tumor characterization and detection in many different organs. In particular, high-b-value DWI (b=2000 s/mm$^2$) combined with T2W MRI are used in some exemplary prostate cancer detection systems.

Some exemplary MRI CAD systems for detecting cancer utilize features derived from T2W MRI and high-b-value DWI. Such systems can extract texture information using local binary pattern (LBP) and variants of LBP. Some embodiments utilize a multi-stage feature selection method that selects the most discriminative features for cancer. In an initial stage, frequent pattern mining discovers a single or a combination of texture patterns that can represent either cancer or benign lesions. In a subsequent stage, a Wilcoxon rank-sum test finds the texture patterns that significantly differ regarding class labels (cancer and benign). In a later stage, the texture patterns that minimize redundancy among the patterns and/or maximize relevance among the patterns and class labels are selected, such as by applying a mutual information-based criterion. The selected patterns can be designated as the most discriminative texture features and can be used to build a classification model, support vector machine (SVM), providing a diagnostic cancer prediction map for the whole organ. This technology can be used for detecting cancer in various organs other than the prostate, such as cancers of the brain, breast, colon, gallbladder, liver, kidneys, lungs, bones, and pancreas.

The foregoing and other objects, features, and advantages of the disclosed technology will become more apparent from the following detailed description, which proceeds with reference to the accompanying figures.

BRIEF DESCRIPTION OF THE DRAWINGS

FIG. 2 is a table providing patient characteristics for an exemplary study.

FIG. 3A is a graph showing single-modal ROC curves for cancer versus MR-positive benign.

FIG. 3B is a graph showing bi- and tri-modal combination ROC curves for cancer versus MR-positive benign.

FIG. 6A shows six false negatives; missed cancer lesions. FIG. 6B shows six false positives; benign lesions that were predicted as cancer are shown.

DETAILED DESCRIPTION

Figure 1:
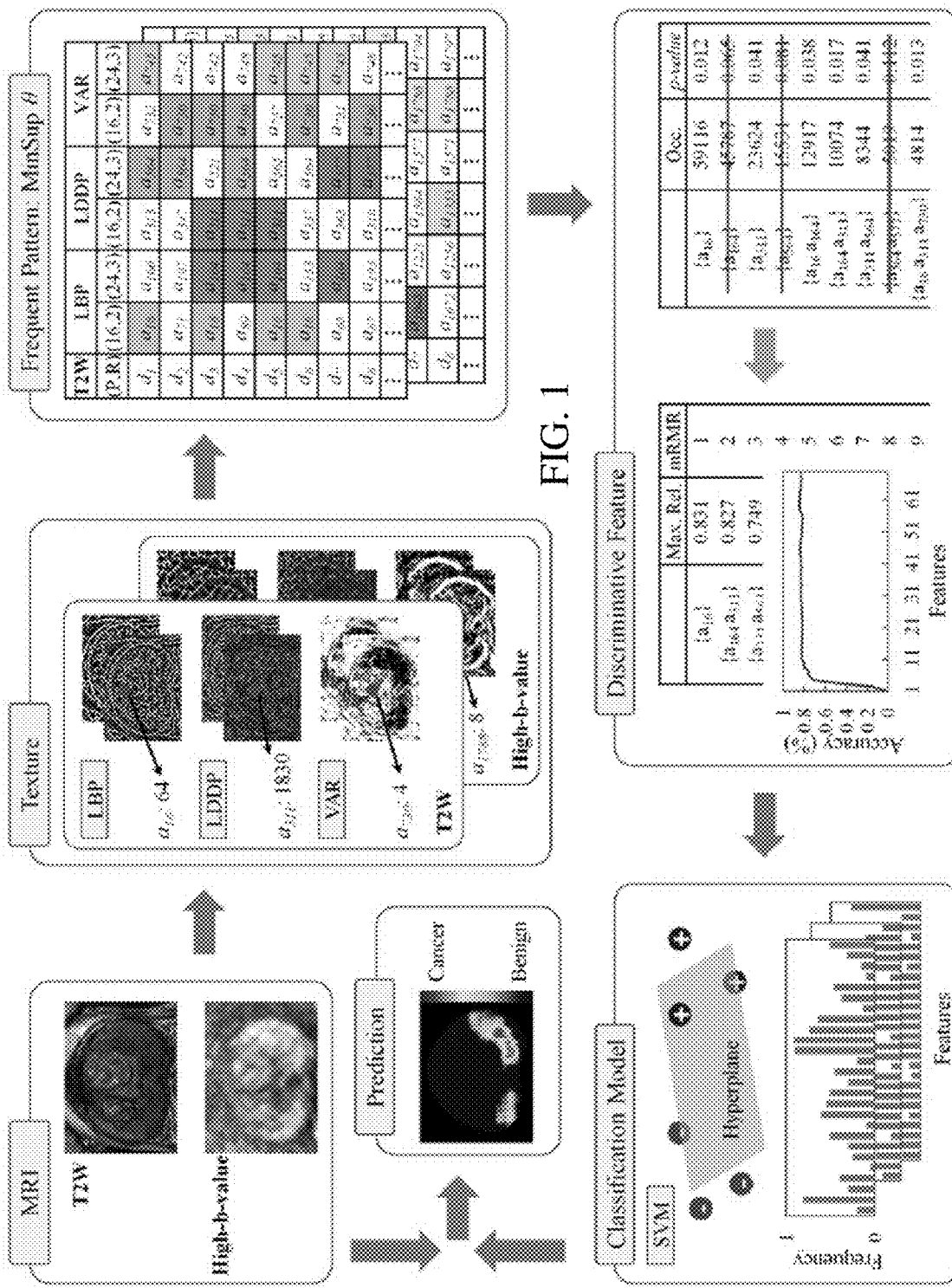
FIG. 1 illustrates an exemplary MRI-based computer aided cancer diagnosis system/method for detecting cancer.

Described herein are methods and systems for detecting or predicting cancer based on imaging data, such as MRI and/or CT imaging data. Exemplary computer aided diagnostic (CAD) systems disclosed herein utilize T2W MRI and high-b-value DWI as inputs. However, alternative CAD systems described herein can utilize various other imaging data inputs, including any combination of imaging modalities described herein or other known imaging modalities. Some exemplary imaging modalities that can be utilized in disclosed CAD systems include T2W MRI, high-b-value DWI, T1-weighted MRI, dynamic contrast enhanced MRI, MRI spectroscopy, diffusion weighted MRI with other b-values, computed tomography, ultrasound, X-ray, SPECT, PET, etc. The term "high-b-value" can mean a b-value of at least 3000 s/mm$^2$, at least 2500 s/mm$^2$, at least 2000 s/mm$^2$, at least 1500 s/mm$^2$, at least 1000 s/mm$^2$, and/or at least 500 s/mm$^2$.

Exemplary Methods and Systems
Exemplary Patient Populations

Eligible patients had a history of elevated PSA or clinical suspicion of prostate cancer and had at least one suspicious lesion visualized on multiparametric MRI. Patients had standard of care 12-core TRUS guided extended sextant biopsies, and two targeted MRI-US fusion guided biopsies (axial and sagittal planes) per MRI-identified lesion. The study population consisted of 508 consecutive patients. Of these, we excluded 264 patients. The characteristics of the remaining 244 patients are presented in FIG. 2.

The 244 patients were divided into calibration and validation datasets. Biopsy-proven MR-identified point targets were used to provide a ground truth label. The calibration dataset was composed of 183 MR-positive lesions consisting of 78 cancers and 105 MR-positive benign lesions derived from MRIs of 108 patients. It was used to select the most discriminative features and to train the CAD system. The validation dataset from 136 patients was composed of 179 MR-positive lesions consisting of 68 cancers and 111 MR-positive benign lesions as well as 117 MR-negative regions sampled by routine biopsy and confirmed to be normal. Two validation studies were performed: (1) cancer vs benign in MR-positive lesions and (2) cancer vs benign in both MR-positive and MR-negative regions. The first validation study was to test that the CAD system is capable of identifying cancerous lesions from benign lesions that were determined as "lesions" by experienced radiologists (68 cancer and 111 benign lesions). The second study was to test that the CAD system can detect cancer lesions from benign lesions whether they were positive or not on MRI (68 cancers, 111 MR-positive benign, and 117 MR-negative benign lesions).

MRI Protocol

Multiparametric MRI of the prostate was performed on a 3-T MR scanner using the anterior half of a 32-channel SENSE cardiac coil and an endorectal coil. The balloon of each endorectal coil was distended with approximately 45 ml of perfluorocarbon to reduce imaging artifacts related to air-induced susceptibility. T2W MRI, DW MRI, and DCE MRI were acquired. Standard DWI was acquired with five evenly spaced b-values (0-750 s/mm$^2$) and high-b-value DWI was acquired with b=2000 s/mm$^2$. Multiparametric MRI was independently evaluated by two experienced genitourinary radiologists. The location of the identified suspicious lesions was recorded in a MRI coordinate system, and imported into a fusion biopsy system. The targets defined by multiparametric analysis were marked on 12W MRI and displayed on triplanar (axial, sagittal, and coronal) images as biopsy targets. In addition, the whole prostate was manually or semi-automatically segmented by the radiologists.

Prostate Biopsy and Review

All patients underwent MRI-US fusion targeted biopsy. During the biopsy, an electromagnetic (EM) field generator was placed above the pelvis, and a 2D end-fire TRUS probe with detachable EM tracking sensors was positioned in the rectum. This enables real-time tracking of the US transducer (and thus biopsy guide and needle path) during the procedure. The operator scanned the prostate from its base to its apex with the tracked probe, and a fan-shaped 3D volumetric US image was reconstructed, segmented, and spatially (rigidly) registered with the prebiopsy T2W MRI which was annotated with targets in a semiautomatic fashion. Then, the live US image was fused with the MR images in real-time. Image registration was based on EM tracking. An experienced prostate pathologist reviewed the biopsy samples, obtained by MRI-US fusion guided biopsy and a standard 12-core systematic biopsy, and reported the tissue characteristics and malignancy.

Exemplary CAD Systems and Methods
Postprocessing

In exemplary methods described herein, T2W MRI data and high-b-value DWI data (or other imaging data sets of different modalities) can initially be normalized. In exemplary methods, potential outliers are identified as the voxels whose intensities are below 1 percentile or above 99 percentile of the voxel intensities in the prostate. Excluding these outlier voxels, we compute the median and standard deviation of the voxel intensities in the prostate using the whole prostate segmentation (semi-automated and confirmed and manually adjusted by the radiologists) and divide the intensity of each voxel by Median+2 x standard deviation. Then, the different modalities of MR images (MRI-to-MRI) can be rigidly registered using MR coordinate information. The image normalization and registration can be performed per MR slice.

Feature Extraction

Three texture operators are incorporated to extract texture information in the prostate: (1) LBP, (2) local direction derivative pattern (LDDP), and (3) variance measure operator (VAR) (FIG. 1). LBP is a popular local texture descriptor due to its low computational complexity, gray-scale and rotation invariance, and robustness to illumination changes. LBP compares the gray level of a pixel and its local neighborhood and generates a (binary) pattern code. The pattern code is often represented as a decimal number. A local neighborhood is defined as a set of evenly distributed pixels on a circle. A radius of the circle determines a spatial resolution of LPB. LDDP is an extension of LBP, which encodes higher order derivative information of texture. VAR measures the local variance of texture. Since VAR is continuous, it is discretized by equal-depth binning to provide a pattern code. Finally, the pattern codes are summarized into a histogram. A bin in the histogram corresponds to a unique pattern code.

Given a (center) pixel c in an image, LBP examines its neighboring pixels $p(p=0, \ldots, P-1)$ in a radius R and generates a binary pattern code as follows $$LBP_{P,R} = \sum_{p=0}^{P-1} s(g_p - g_c)2^p,$$

where s(x) is 1 if x≥0 and 0 if x<0 and $g_c$ and $g_p$ represent the gray level of the center pixel and its neighborhood pixels, respectively. The coordinates of the neighborhood pixels are computed as (R cos(2πp/P), −R sin(2πp/P)) and their gray levels are estimated by interpolation. Since LBP depends exclusively on the sign of the gray level differences, the pattern code is invariant to the scaling of the gray scale. Moreover, rotating the image, the gray level of the neighborhood pixels rotates around the center pixel. The rotation results in a different binary pattern code but only makes a bitwise shift in the original pattern code. Hence, rotation-invariant pattern code is computed as $$LBP^{ri}_{P,R} = \min\{ROR(LBP_{P,R},i)|i=0,1,\ldots P-1\},$$

where ROR(x, i) is a circular bitwise shift operator on x by I bits.

Higher order derivative information is computed using LDDP (Ref. 38) to provide more detailed texture information. Second order LDDP along p direction is computed as follows:

$$LDDP^2_{P,R} = \sum_{p=0}^{P-1} s(d^2_{p,R})2^p$$

$$d^2_{p,R} = (g_p^{R_2} - g_p^{R_1}) - (g_p^{R_1} - g_c) = g_p^{R_2} + g_c - 2g_p^{R_1}.$$

where $g_p^{R_1}$ and $g_p^{R_2}$ denote the gray level of a neighborhood pixel p in a circle of radius $R_1$ and $R_2$, respectively.

Since LBP and LDDP lack contrast information, variance of the local contrast is also measured as follows:

$$VAR_{P,R} = \frac{1}{P}\sum_{p=0}^{P-1}(g_p - \mu)^2,$$

where $$\mu = \frac{1}{P}\sum_{p=0}^{P-1} g_p.$$

Feature Selection

When multiple LBPs with various radii and/or LBP variants (e.g., LDDP and VAR) are incorporated, a multidimensional histogram outperforms a combination of single histograms. However, the multidimensional histogram is not time- and space-effective due to the exponential growth of feature space. Furthermore, many noisy bins adversely affect the texture analysis since their density estimates are unreliable. Limiting the number of bit transitions (from 0 to 1, or vice versa), "uniform" patterns are often utilized but lead to a huge loss of texture information. Instead, we find the most informative histogram bins (or features) that are frequent and discriminative, i.e., improve discriminative power as well as reduce noisy bins.

First, we find frequent pattern codes by adopting a data mining approach, so called frequent pattern mining. Whether a pattern code is frequent or not is determined by a user-specified threshold. Frequent pattern mining discovers any combination of the pattern codes that are frequent, i.e., it simultaneously examines not only an individual operator (single-dimensional histograms) but also any combinations of the operators (multi-dimensional histograms). Hence, "frequent pattern codes" include bins from single- and multiple-operator histograms. Second, the occurrences of the frequent pattern codes between cancers and benign tissue are compared using Wilcoxon rank-sum test. Only the significant pattern codes (p-value<0.05) are selected. Third, the significant pattern codes are ordered via mRMR (minimum redundancy maximum relevance) criterion. Following the mRMR order, forward feature selection sequentially adds one new pattern code at a time, and measures the discriminative power of the pattern codes so far, at that point in time. The set of pattern codes with the highest classification performance is chosen as the most discriminative pattern set. Performing K-fold cross validation, the classification performance is measured by the ratio of the number of correctly predicted cancers and benign cases and the total number of cases. K-fold cross validation divides the training dataset into K disjoint partitions, learns classification models on the K−1 partitions, and tests the models on the remaining partition. This is repeated K times with different choices of the testing partition. We set K=5. The frequency of the most discriminative pattern codes forms the texture features for the CAD system.

Frequent Pattern Mining

Suppose a dataset D={$d_1,d_2,\ldots,d_n$} has NA categorical attributes, and class label Y={$y_1, y_2, \ldots, y_n$} had $N_c$ classes where $y_i$ is the label associated with data $d_i$. Each attribute could have a number of values, and each pair of an attribute A and a value v (A, v) is mapped to a distinct item in Q={$a_1, a_2,\ldots,a_m$}. Then, each data $d_i$ is represented as a set of items in Q. In the dataset, frequent patterns are the item sets which occur no less than a user-specified predetermined threshold. In other words, a k-item set α, consisted of k items from Q, is frequent if α occurred no less than θ |D| times in the dataset, where θ is a user-specified minimum support (Min-Sup) threshold, |D| is the total number of data, and the support of a pattern is the number of data containing the pattern (MinSup=1%). "FP-growth," which generates the complete set of frequent patterns without candidate generation, is used to mine frequent patterns.

mRMR

Minimum redundancy maximum relevance (mRMR) is a feature selection method that attempts not only to maximize the relevance between the features and class labels but also to minimize the redundancy among the features. Both the relevance and redundancy are characterized in terms of mutual information as follows:

$$\text{maximal relevance: } \max D(S, c), \quad (6)$$

$$D = \frac{1}{|S|}\sum_{x_i \in S} I(x_i; Y),$$

$$\text{minimal redundancy: } \min R(S),$$

$$R = \frac{1}{|S|^2}\sum_{x_i, x_j \in S} I(x_i; x_j),$$

where I (x; y) represent the mutual information of two variables x and y, S is a feature set, and Y is a class label. To achieve the goal of optimizing the above two conditions simultaneously, the simple mRMR criterion, max(D−R), is invoked. mRMR starts from a feature with the highest maximal relevance and selects a new feature among the rest of features that is the most correlated with the class labels while being the least redundant with the selected features so far. Thus, it generates an order of the features according to the mRMR criterion.

Classification

For each MRI, the three texture operators (LBP, LDDP, and VAR) are applied using two neighboring topologies (P,R)={(16,2), (24,3)}, i.e., six different pattern codes are generated for each pixel. Collecting pattern codes in a rectangular window (7×7 mm) centered at the MRI-identified target point, the discriminative texture features are selected and computed using a three-stage feature selection method (frequent pattern mining, Wilcoxon rank-sum test, and mRMR criterion). SVM (Ref. 35) [LIBSVM (Ref. 42) implementation in $_{MATLAB}$] is used to distinguish cancer (+1) from benign (−1) lesions. As a kernel function, a radial basis function K $(x_i, x_j)=\exp(-\gamma \|x_i - x_j\|^2)$, $\gamma=1$ is adopted. The classification results are summarized into a receiver operating characteristic (ROC) curve. The area under ROC curve (AUC) and a 95% confidence interval (CI) are computed with the trapezoidal rule. Sensitivity (the rate of correctly identified cancer lesions given true cancer lesions) and specificity (the rate of correctly identified benign lesions given true benign lesions) are also computed using zero as the cutoff value.

Statistical Analysis

Statistical significance of frequent patterns in discriminating cancer lesions from benign lesions is determined by Wilcoxon rank-sum test. Boot-strap resampling with 2000 repetitions is adopted to assess 95% CI of AUCs and statistical significance of the differences between AUCs of the two ROC curves.

Results and Discussion

Figures 4A, 4B:
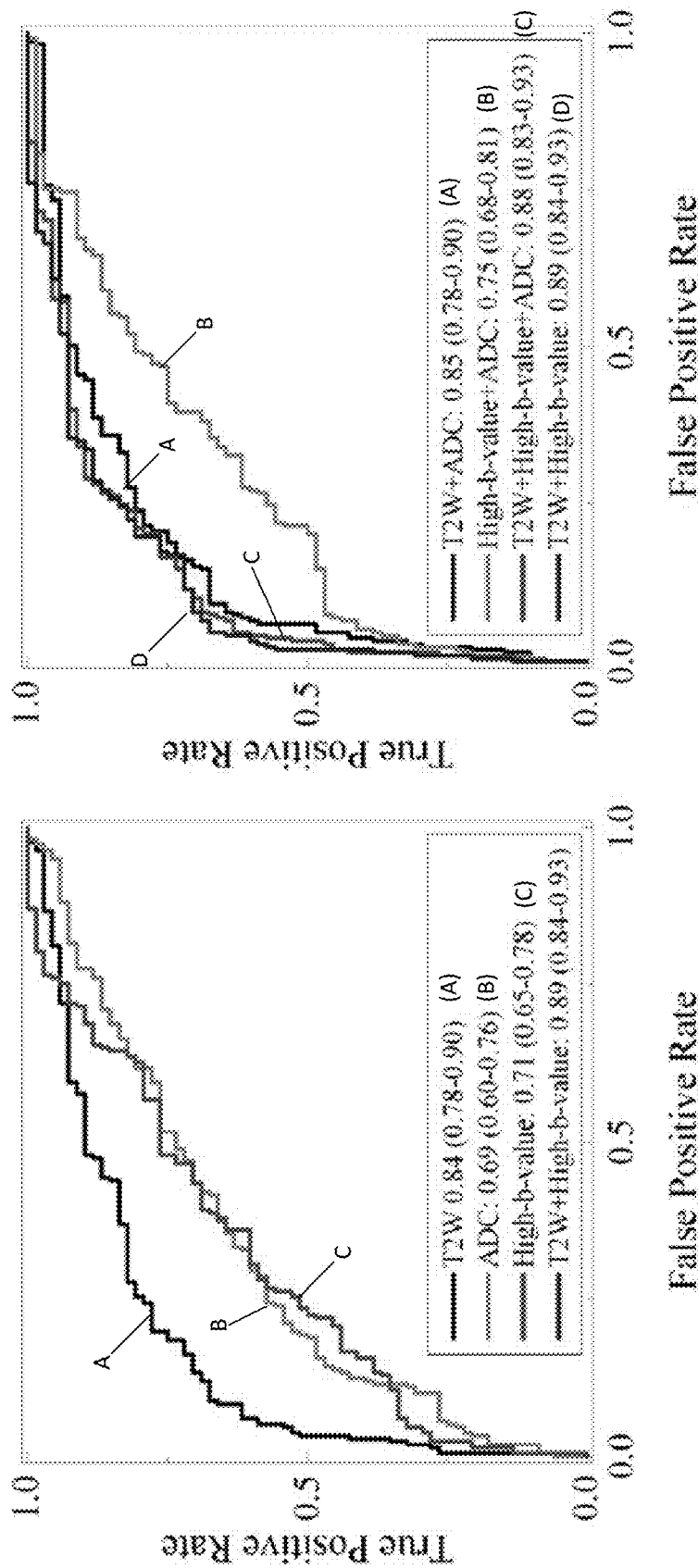
FIG. 4A is a graph showing single-modal ROC curves for cancer versus benign.
FIG. 4B is a graph showing bi- and tri-modal combination ROC curves for cancer versus benign.

We trained our CAD system using the discriminative features from T2W MRI and high-b-value DWI [calibration performance: 0.97 AUC (95% CI: 0.94-0.99)]. Then, the two validation studies were performed. In the first validation study (cancer vs MR-positive benign), our CAD system achieved an AUC of 0.83 (95% CI: 0.76-0.89) [FIG. 2(b)]. An AUC of 0.89 (95% CI: 0.84-0.93) was obtained in the second validation study [cancer vs benign (MR-positive or MR-negative)] [FIG. 3(b)]. Moreover, the cancer prediction of our CAD system was not dependent on the specific regions of the prostate [peripheral zone: 0.83 AUC (0.73-0.91 95% CI) and transition zone: 0.83 AUC (0.72-0.93 95% CI)]. The CAD system predicted the presence of cancer for the whole prostate. The predicted cancer areas corresponded to the MR suspicious lesions that were proved to be cancer by MRI-US fusion targeted biopsy and pathology review [FIG. 4(a)]. The MR-positive benign areas were predicted as benign [FIG. 4(b)].

Figure 5A:
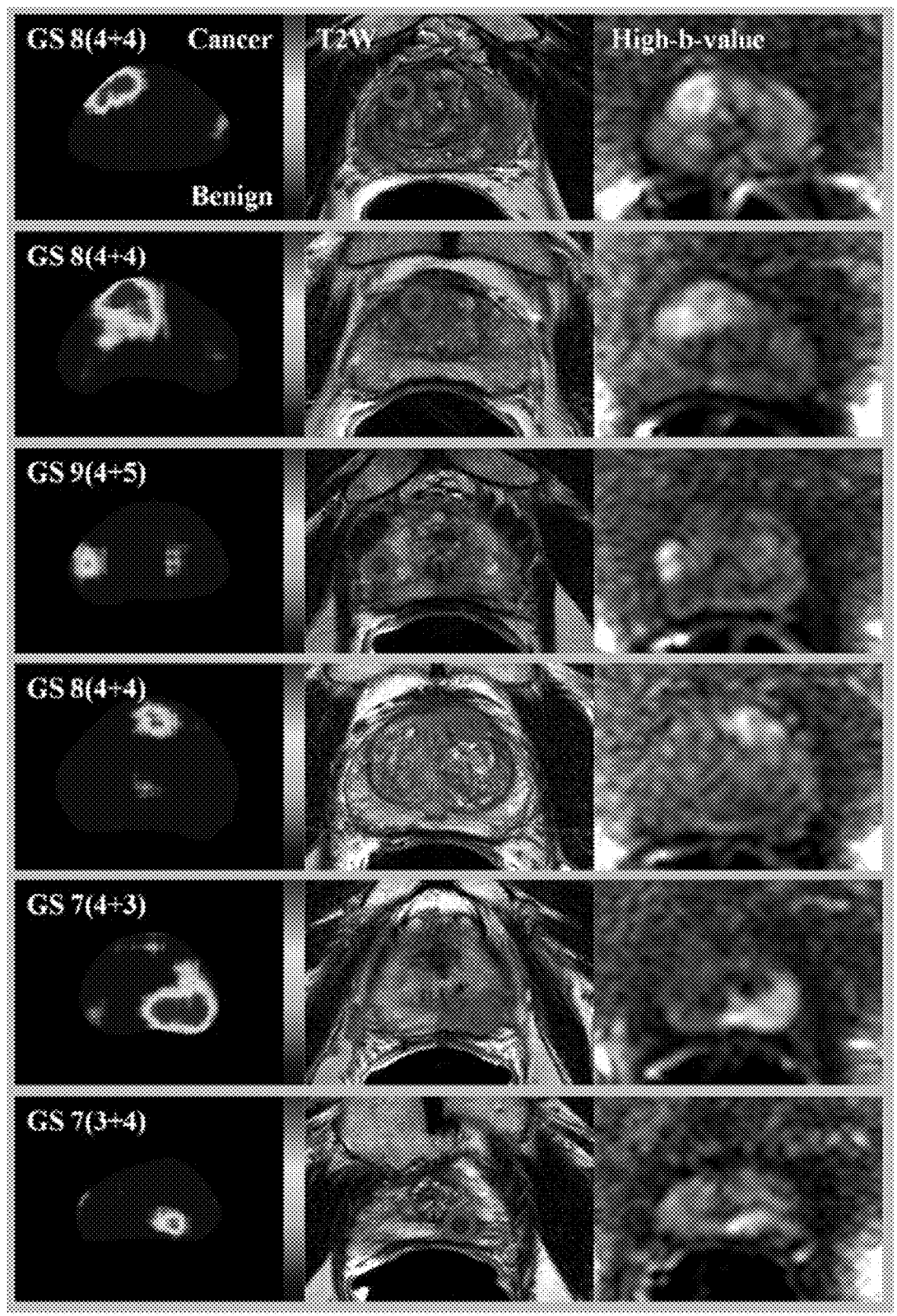
FIGS. 5A and 5B illustrate cancer prediction for the whole prostate from 12 different patients (each row is for one patient). The first, second, and third columns (from left to right) show a cancer prediction map, T2W MRI, and high-b-value DWI, respectively. MR-positive lesions (red circles) were proven to be cancer for the six patients in FIG. 5A, and were proven to be benign for the six patients in FIG. 5B.
Figure 5B:
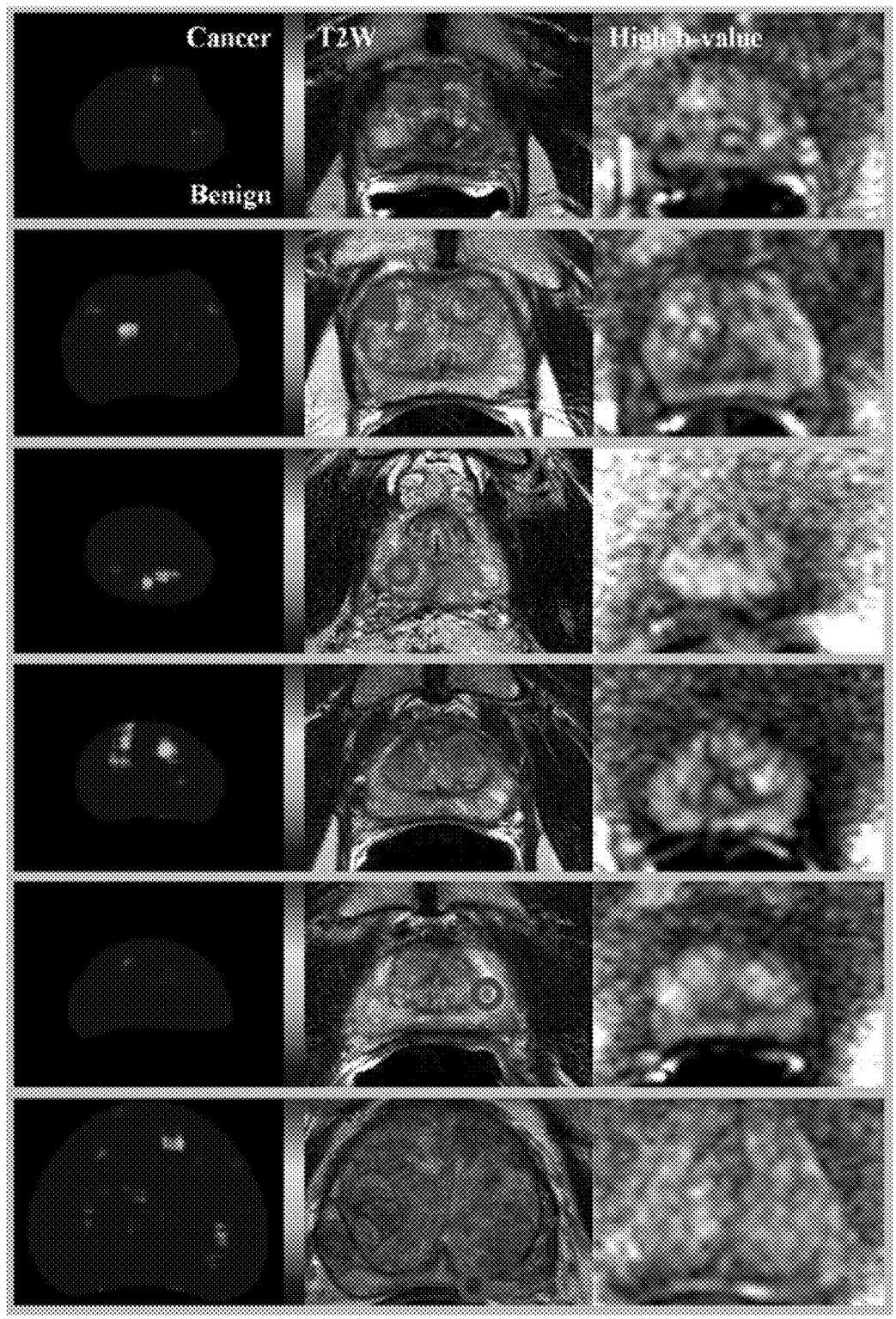
Figure 6A:
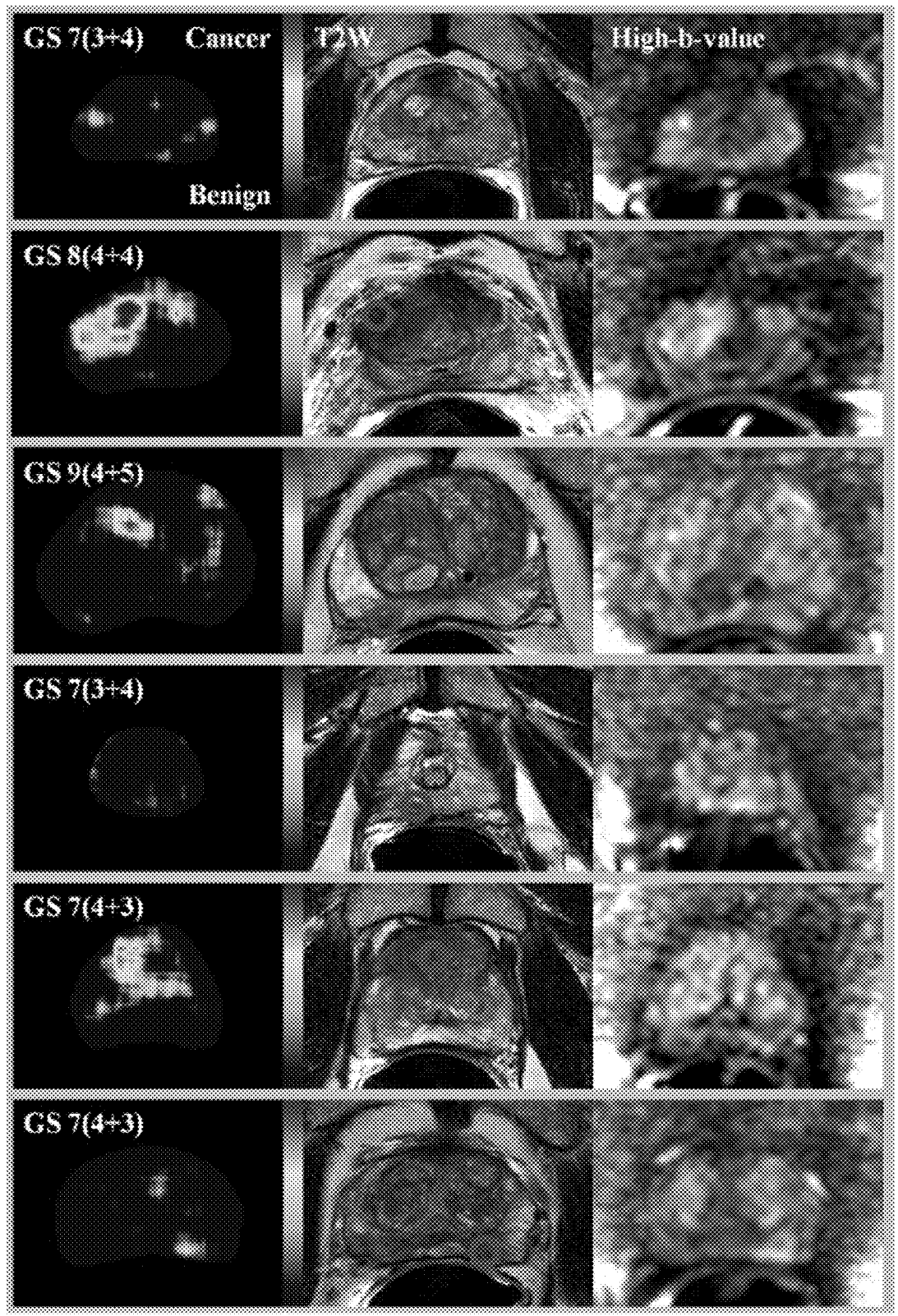
FIGS. 6A and 6B illustrate false prediction from 12 different patients (each row is for one patient). The first, second, and third columns (from left to right) show a cancer prediction map, T2W MRI, and high-b-value DWI, respectively. Red circles are MR-positive lesions.
Figure 6B:
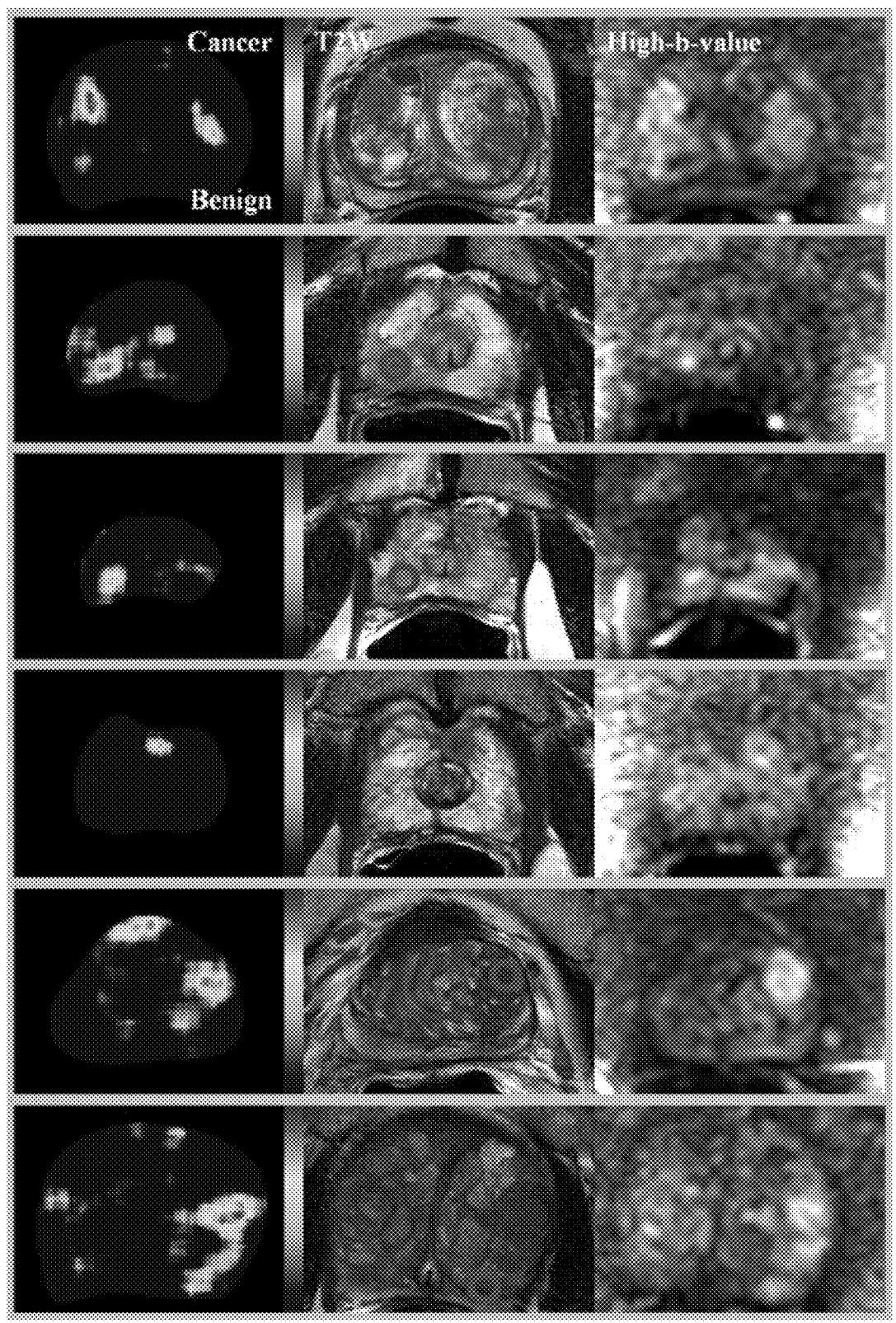

We also assessed mispredicted cases (false negatives and false positives) by our CAD system. False negatives, missed cancer lesions, mainly included smaller or subcapsular lesions [rows 1, 3, 4, and 6 in FIG. 5(a)]. Due to the window-based feature computation scheme, insufficient information may have provided and complicated the prediction, leading to a lower likelihood of cancer. In some cases, although the targeted voxel was missed, its neighboring voxels were correctly identified as cancer [rows 2 and 5 in FIG. 5(a)]. Moreover, false positives, benign lesions that were predicted as cancer, were often observed where cancerlike imaging signatures are shown: dark on T2W MRI and bright on high-b-value DWI [FIG. 5(b)]. BPH [row 3 in FIG. 5(a) and rows 1, 5, and 6 in FIG. 5(b)] and dark anterior areas [row 5 in FIG. 5(b)] were other causes of false positives.

We repeated the two validation experiments using each of the two MRI modalities (T 2W MRI and high-b-value DWI) and the ADC map of the standard DWI. For the discrimination of cancer and MR-positive benign lesions, T2W MRI, high-b-value DWI, and the ADC map alone showed an AUC of 0.78 (95% CI: 0.70-0.85), 0.65 (95% CI: 0.56-0.73), and 0.67 (95% CI: 0.59-0.75), respectively [FIG. 2(a)]. For cancer vs benign, T2W MRI achieved an AUC of 0.84 (95% CI: 0.78-0.90), high-b-value DWI achieved an AUC of 0.71 (95% CI: 0.64-0.78), and the ADC map achieved an AUC of 0.69 (95% CI: 0.60-0.76) [FIG. 3(a)]. There were significant differences between our CAD system and these single-modal predictions.

Additionally, bi- and tri-modal combinations were tested. The combination of T2W MRI and the ADC map showed the AUCs of 0.78 (95% CI: 0.71-0.85) and 0.85 (95% CI: 0.78-0.90) for cancer vs MR-positive benign and for cancer vs benign, respectively. The combination of high-b-value DWI and the ADC map produced an AUC of 0.69 (95% CI: 0.60-0.77) for cancer vs MR-positive benign and an AUC of 0.75 (95% CI: 0.68-0.81) for cancer vs benign. The differences between these two bimodal combinations and our CAD system were also statistically significant. Interestingly, the tri-modal combination, combining T2W MRI, high-b-value DWI, and the ADC map, did not improve upon our CAD system utilizing T2W MRI and high-b-value DWI. There was no statistically significant difference between them.

Using the three-stage feature selection scheme, 124 discriminative features were obtained. The features were from 48 different combinations of the three texture operators and two neighboring topologies. The length of the pattern codes forming the discriminative features ranged from 1 to 6. Hence, the feature selection method, in fact, explored a variety of combinations and selected the features that best describe the texture information of cancer and benign lesions.

The results of our study demonstrated that an MRI CAD system combining T2W MRI and high-b-value DWI can identify cancer for the whole prostate and the three-stage feature selection scheme can find the most discriminative texture features for distinguishing cancer and benign lesions. The discriminative features were selected from a variety of combinations of texture patterns, which are infeasible with the conventional approach of constructing multiple single- or multi-dimensional histograms; for instance, a 6D histogram would require >20×106 bins with the same setting. This CAD system can distinguish cancer from MR-positive benign lesions that were preselected by expert radiologists, illustrating how the CAD system can reduce the number of negative biopsies.

An exemplary CAD system as described herein was independently trained and tested on a large-scale dataset including 244 patients. The training and validation datasets contained a diverse population of at risk patients with differing frequencies of cancer and benign lesions (Table I). At 70% specificity, our CAD system showed 72% and 88% sensitivity for cancer vs MR-positive benign and cancer vs benign, respectively. In addition, we have developed another CAD system utilizing T 2W MRI, the ADC map of DWI, and DCE MRI on the overlapping patient population. A random forest classifier was built using first/second order statistics, texture, and shape features. Instead of point targets, contours of targeted lesions were identified by expert radiologists and used to train (40 patients) and test (21 patients) the classifier. An AUC of 0.928 (CI: 0.927-0.928)

was achieved. Adding DCE MRI, the CAD system improved the performance of cancer detection.

MRIs with a substantial patient motion or deformation can cause negative effects on the classification model. Since discriminative features can be computed from a rectangular window of 7×7 mm around a targeted voxel, for example, a slight patient movement, even a few millimeters, during imaging acquisition can have a significant impact on feature computation. However, local deformations or displacements of the prostate may occur in the clinics. Image registration algorithms can be used to correct for such motion or deformation, enabling better registration of MRI sequences and improved performance of the CAD system.

In disclosed systems, three texture operators of one particular type can be incorporated in a CAD system. Combined with other intensity- or texture-based features, alternative CAD system can provide a more accurate and reliable prediction.

Some alternative CAD systems incorporate DCE MRI and/or MR spectroscopy to improve the CAD system. DCE MRI can include a gadolinium-based contrast injection.

The additive value of the disclosed CAD systems to current clinical practices can be significant. Disclosed CAD systems can facilitate biopsy in clinical settings as the cancer prediction of the CAD system can help to improve performance in identifying clinically significant prostate cancers and can improve the diagnostic yield, workflow and throughput of prostate biopsy.

The ability to assist readers of prostate MRI and other organ MRI with cancer prediction maps, or other diagnostic information, can improve the diagnostic yield of prostate biopsy and can help surgical- or therapeutic-planning of prostate cancer as well as assisting nonspecialists in interpreting prostate MRI, making these methods available to a wider population, while potentially reducing the learning curve for interpretation training.

Exemplary Methods

Figure 7:
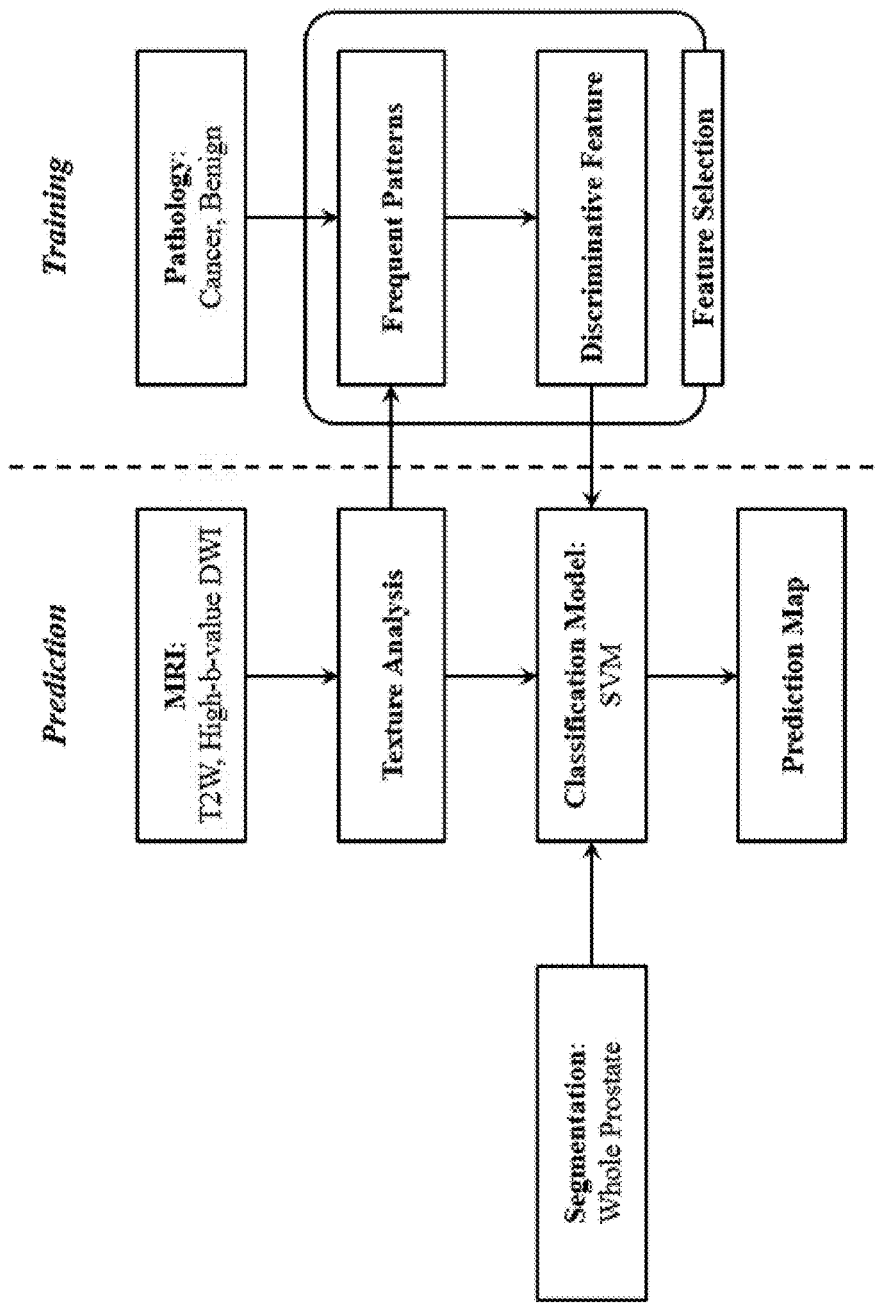
FIG. 7 is a flow chart illustrating an exemplary method including a training phase and a prediction phase.

FIG. 7 is a flow chart illustrating the interplay between the training and prediction aspects of the disclosed technology. The prediction aspect begins with both T2W and High-b-value DWI input datasets, applies texture analysis to the input datasets, generates a classification model using SVM, and outputs diagnostic information, such as a cancer predication map of the whole prostate or other organ. In the texture analysis phase, the method searches for discriminative features derived using frequent pattern mining and/or other tools during the training phase, and the selected features found and identified are used to generate the classification model and prediction map.

Figure 8:
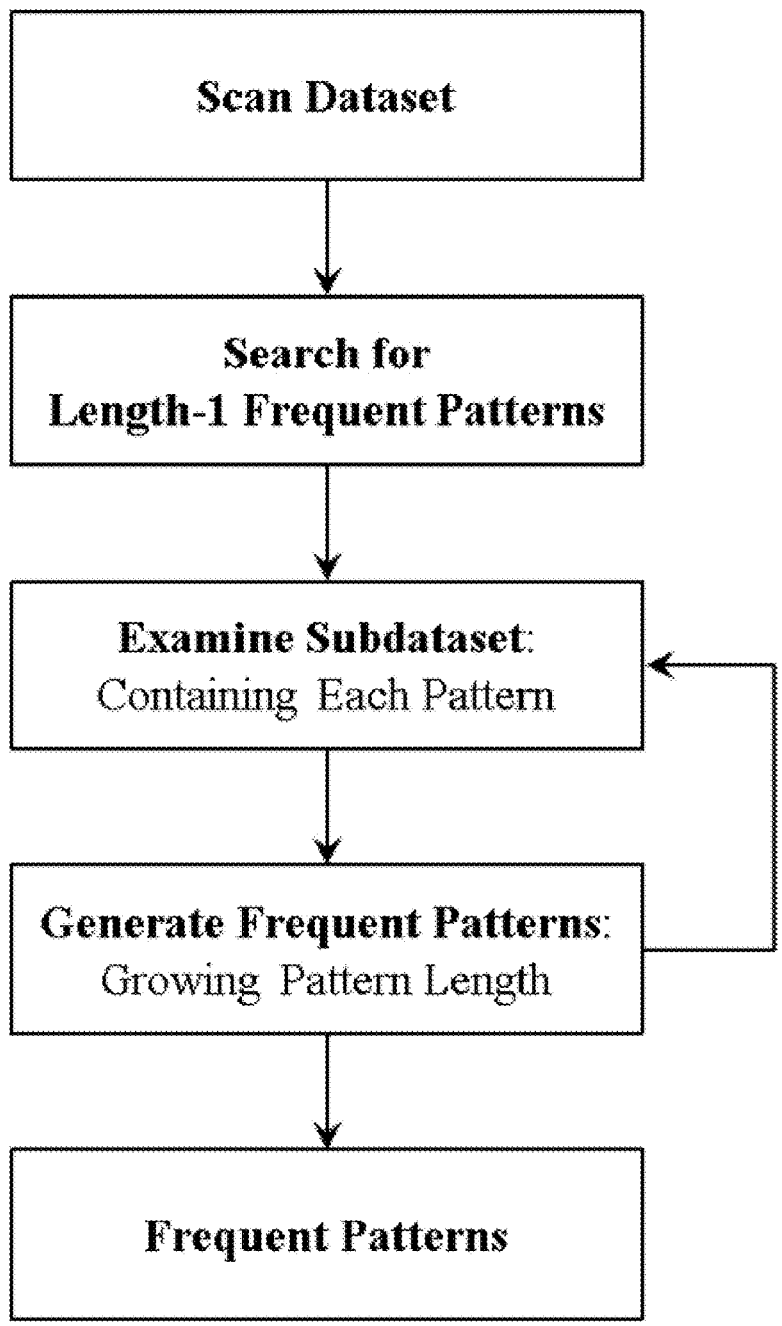
FIG. 8 us a flow chart illustrating an exemplary method for frequent pattern mining.

The input dataset or datasets used in such a method can comprise a number of MR voxels. Each MR voxel can contain a number of values representing a unique texture pattern code. This texture information can be extracted from the input datasets prior to determining the texture features that are indicative of cancer. Determining the texture features that are indicative of cancer can include several steps, including utilizing discriminative features from frequent pattern mining. A frequent pattern can denote a texture pattern code or a combination of texture pattern codes that occurs more that a predetermined (e.g., user-specified) threshold value, such as more than 1% of the entire data set. Such frequent patterns can be determined using frequent pattern mining. As illustrated in FIG. 8, frequent pattern mining can comprise scanning the entire dataset(s), searching for and identifying length-1 frequent patterns (e.g., single texture pattern codes), examining a sub-dataset that contains each identified frequent pattern, generating frequent patterns with increasingly longer pattern lengths, and repeating the examining and generating steps a sufficient number of times to produce a sufficient set of frequent patterns. A "length-1" frequent pattern or pattern code is a frequently occurred pattern associated with a single image processing operator (e.g., LBP, LDDP, VAR, etc.) that is applied to an image location. When two or more (e.g., N) image processing operators are applied (e.g., LBP+LDDP, LBP+VAR, etc.), the result is a length-2 (or length-N) frequent pattern or pattern code, which are frequent patterns or pattern codes with increased pattern lengths relative to a length-1 pattern. Frequent patterns with increasing pattern length generate increasingly higher dimensional texture information. During frequent pattern mining, the frequency of several, or all, possible pattern combinations of several, or all, different pattern lengths can be calculated.

A computer or other processing system comprising a processor and memory, such as a personal computer, a workstation, a mobile computing device, or a networked computer, can be used to perform the methods disclosed herein, including any combination of MR imaging acquisition, imaging processing, imaging data analysis, data storage, and output/display of results (e.g., cancer prediction maps, etc.). The computer or processing system may include a hard disk, a removable storage medium such as a floppy disk or CD-ROM, and/or other memory such as random access memory (RAM). Computer-executable instructions for causing a computing system to execute the disclosed methods can be provided on any form of tangible and/or non-transitory data storage media, and/or delivered to the computing system via a local area network, the Internet, or other network. Any associated computing process or method step can be performed with distributed processing. For example, extracting texture information from the imaging data and determining texture features that are indicative of cancer can be performed at different locations and/or using different computing systems.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A method for facilitating cancer diagnosis, comprising:
    extracting texture information from imaging data for a target organ;
    determining texture features that are indicative of cancer by identifying frequent texture patterns in the extracted texture information by:
        (1) identifying frequent texture patterns from the extracted texture information using frequent pattern mining by:
            (a) identifying length-1 frequent patterns in the extracted texture information that are represented by a single texture pattern code that occurs more than a predetermined threshold percentage of the entire dataset,
            (b) examining sub-datasets of the extracted texture information, wherein each sub-dataset contains a different one of the identified length-1 frequent patterns,
            (c) generating frequent patterns with increasing pattern length, and
            (d) examining additional sub-datasets of the extracted texture information, wherein each additional sub-dataset contains a different one of the generated frequent patterns having the increased pattern length;
        (2) comparing occurrences of the frequent texture patterns between cancers and benign tissue using a Wilcoxon rank-sum test and selecting significant texture patterns based on the comparison; and
        (3) ordering the significant texture patterns using minimum redundancy maximum relevance (mRMR) criterion, and then choosing the most discriminative texture features using forward feature selection;
    generating a classification model based on the determined texture features that are indicative of cancer; and
    based on the classification model, generating diagnostic cancer prediction information for the target organ.

2. The method of claim 1, wherein the imaging data is derived from high-b-value diffusion weighted MRI.

3. The method of claim 1, wherein the imaging data is derived from T2-weighted MRI.

4. The method of claim 1, further comprising extracting texture information from first imaging data for a target organ and second imaging data for the target organ, the first and second imaging data being derived from different imaging modalities.

5. The method of claim 4, wherein the first imaging data is derived from high-b-value diffusion weighted MRI and the second imaging data is derived from T2-weighted MRI.

6. The method of claim 4, further comprising normalizing and registering the first imaging data and the second imaging data prior to applying the classification model.

7. The method of claim 1, wherein the extraction of texture information is performed using local binary pattern (LBP), local direction derivative pattern (LDDP), and variance measure operator (VAR).

8. The method of claim 1, wherein the classification model is generated using support vector machine (SVM).

9. The method of claim 1, wherein generating diagnostic cancer prediction information comprises generating a cancer prediction map for the target organ.

10. A computing system for cancer diagnosis, the system comprising a processor and memory, the system operable to:
    extract texture information from first imaging data for a target organ;
    based on the extracted texture information, determine texture features that are indicative of cancer by:
        identifying frequent texture patterns from the extracted texture information using frequent pattern mining by:
            (a) identifying length-1 frequent patterns in the extracted texture information that are represented by a single texture pattern code that occurs more than a predetermined threshold percentage of the entire dataset,
            (b) examining sub-datasets of the extracted texture information, wherein each sub-dataset contains a different one of the identified length-1 frequent patterns,
            (c) generating frequent patterns with increasing pattern length, and
            (d) examining additional sub-datasets of the extracted texture information, wherein each additional sub-dataset contains a different one of the generated frequent patterns having the increased pattern length;
        comparing occurrences of the frequent texture patterns between cancers and benign tissue using a Wilcoxon rank-sum test and selecting significant texture patterns based on the comparison; and
        ordering the significant texture patterns via minimum redundancy maximum relevance (mRMR) criterion;
    generate a classification model based on the determined texture features that are indicative of cancer; and
    based on the classification model, generate a diagnostic cancer prediction map of the target organ.

11. The system of claim 10, wherein the first imaging data is derived from high-b-value diffusion weighted MRI.

12. The system of claim 10, wherein the first imaging data is derived from T2-weighted MRI.

13. The system of claim 10, wherein the system is operable to receive second imaging data for the target organ, the first and second imaging data being from different imaging modalities.

14. The system of claim 13, wherein the first imaging data is derived from high-b-value diffusion weighted MRI and the second imaging data is derived from T2-weighted MRI.

15. The system of claim 13, wherein the system is operable to normalize and register the first and second imaging data prior to extracting texture information.

16. The system of claim 10, wherein the texture information is extracted using local binary pattern (LBP), local direction derivative pattern (LDDP), and variance measure operator (VAR).

17. The system of claim 10, wherein the classification model is generated using support vector machine (SVM).

18. The system of claim 10, wherein the target organ is a human prostate.

19. One or more non-transitory computer readable media storing computer-executable instructions, which when executed by a computer cause the computer to perform the method of claim 1.

* * * * *